United States Patent [19]

Schmiechen et al.

[11] 4,012,495
[45] Mar. 15, 1977

[54] 4-(POLYALKOXYPHENYL)-2-PYRROLI-DONES

[75] Inventors: Ralph Schmiechen; Reinhard Horowski; Dieter Palenschat; Gert Paschelke; Helmut Wachtel; Wolfgang Kehr, all of Berlin, Germany

[73] Assignee: Schering Aktiengesellschaft, Berlin & Bergkamen, Germany

[22] Filed: Mar. 20, 1975

[21] Appl. No.: 560,193

[30] Foreign Application Priority Data

Mar. 20, 1974 Germany ........................... 2413935

[52] U.S. Cl. .......................... 424/274; 424/248.58; 424/250; 424/267; 260/247.1 M; 260/247.2 A; 260/246 B; 260/268 H; 260/293.64; 260/293.71; 260/326.5 FL; 260/326.5 S; 260/326.45; 260/326.47; 260/326.37; 424/248.54; 424/248.55; 424/248.56

[51] Int. Cl. ....................................... A61k 31/40

[58] Field of Search ............ 260/326.5 FL, 326.5 S; 424/274, 267

[56] References Cited
FOREIGN PATENTS OR APPLICATIONS 1,140,188  1/1969  United Kingdom

*Primary Examiner*—Alton D. Rollins
*Assistant Examiner*—Mark L. Berch
*Attorney, Agent, or Firm*—Millen & White

[57] ABSTRACT

4-(Polyalkoxyphenyl)-2-pyrrolidones of the formula

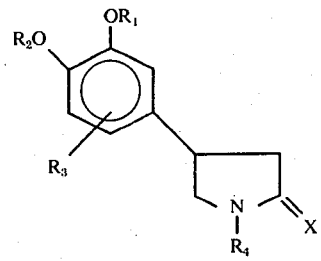

wherein $R_1$ and $R_2$ each are hydrocarbon of up to 18 carbon atoms or alkyl of 1–5 carbon atoms substituted by halogen, OH, COOH, alkoxy, alkoxycarbonyl, carboxamido or amino or collectively are alkylene of 1–3 carbon atoms, $R_3$ is H or $OCH_3$, $R_4$ is H, alkyl, aryl or acyl and X is O or S possess neuropsychotropic activity. The compounds wherein X is O are produced by saponifying and decarboxylating a corresponding 2-pyrrolidone-3-carboxylic acid alkyl ester or cyclizing a corresponding 3-phenyl-4-aminobutyric acid or alkyl ester thereof. The pyrrolidones are converted to corresponding thiopyrrolidones in a conventional manner, e.g., by reaction with phosphorous pentasulfide in the presence of base.

58 Claims, No Drawings

4-(POLYALKOXYPHENYL)-2-PYRROLIDONES

BACKGROUND OF THE INVENTION

This invention relates to novel 4-polyalkoxyphenyl)-2-pyrrolidones.

SUMMARY OF THE INVENTION

In a composition aspect, this invention relates to racemic and optically active 4-(polyalkoxyphenyl)-2-pyrrolidones of general Formula I

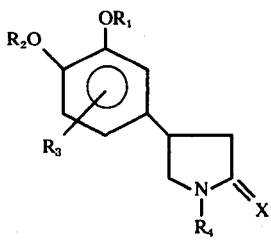

wherein $R_1$ and $R_2$ each are alike or different and are hydrocarbon of up to 18 carbon atoms or alkyl of 1–5 carbon atoms which are substituted by one or more of halogen atoms, hydroxy, carboxy, alkoxy, alkoxycarbonyl, carboxamide and amino or substituted amino or collectively are alkylene of 1–3 carbon atoms; $R_3$ is a hydrogen atom or methoxy; $R_4$ is a hydrogen atom, alkyl, aryl or acyl; X is an oxygen atom or a sulfur atom.

In another composition aspect, this invention relates to pharmaceutical compositions comprising one or more compounds of Formula I in admixture with a pharmaceutical carrier.

In process aspects, this invention relates to processes for the production of compounds of Formula I and to methods of using them.

DETAILED DISCUSSION

The compounds of general Formula I possess an asymmetrical carbon atom. Thus, they can be present both as racemates and as optical antipodes thereof.

Examples of hydrocarbon $R_1$ and $R_2$ groups are saturated and unsaturated, straight-chain and branched alkyl of 1–18, preferably 1–5, carbon atoms, cycloalkyl and cycloalkylalkyl, preferably of 3–7 carbon atoms, and aryl and aralkyl, preferably of 6–10 carbon atoms, especially monocyclic.

Examples of alkyl are methyl, ethyl, propyl, isopropyl, butyl, isobutyl, tert.-butyl, pentyl, 2-methylbutyl, 2,2-dimethylpropyl, hexyl, heptyl, octyl, nonyl, 1,2-dimethylheptyl, decyl, undecyl, dodecyl and stearyl. Examples of unsaturated alkyl groups are alkenyl and alkinyl, e.g., vinyl, 1-propenyl, 2-propenyl, 2-propinyl and 3-methyl-2-propenyl. Examples of substituted alkyl groups, preferably of 1–5 carbon atoms, are those mono- or polysubstituted, for example, by halogen, especially fluorine, chlorine and bromine. Specific examples of such halogen-substituted alkyl are 2-chloroethyl, 3-chloropropyl, 4-bromobutyl, difluoromethyl, trifluoromethyl, 1,1,2-trifluoro-2-chloroethyl, 3,3,3-trifluoropropyl, 2,2,3,3,3-pentafluoropropyl and 1,1,1,3,3,3-hexafluoro-2-propyl. Examples of other suitable substituents for such alkyl groups are hydroxy groups, e.g., 2-hydroxyethyl or 3-hydroxypropyl; carboxy groups, e.g., carboxymethyl or carboxyethyl; alkoxy groups, wherein each alkoxy group contains 1–5 carbon atoms, e.g., ethoxymethyl, isopropoxymethyl, 2-methoxyethyl, 2-isopropoxyethyl, 2-butyoxyethyl, 2-isobutoxyethyl, 3-pentoxypropyl.

Also suitable as preferably terminal-positioned substituents on alkyl groups of 1–5 carbon atoms are alkoxycarbonyl of 1–5 carbon atoms in the alkoxy group and carboxamido wherein the nitrogen atom is unsubstituted or mono- or disubstituted by alkyl of preferably 1–5 carbon atoms or wherein the nitrogen atom is a ring member of a 4- to 7-membered ring. Specific examples of such alkoxycarbonyl and carboxamido groups are ethoxycarbonylmethyl, 2-butoxycarbonylethyl, diethylaminocarbonylmethyl, 2-diethylaminocarbonylethyl, 2-pyrrolidinocarbonylethyl and piperazinocarbonylmethyl.

Alkyl groups of 1–5 carbon atoms can also be substituted, e.g., in the $\beta$, $\gamma$ and preferably terminal position with amino groups wherein the nitrogen atom optionally is mono- or disubstituted by alkyl, preferably of 1–5 carbon atoms, or is part of a 4- to 7-membered ring. Specific examples of N-substituted alkyl groups are aminomethyl, 2-methylaminoethyl, 2-dimethylaminoethyl, 2-diethylaminoethyl, 3-dimethylaminopropyl, 3-ethylmethylaminopropyl, pyrrolidino, piperidino, morpholino, N-methylpiperazino and hexamethylenimino.

When $R_1$ and/or $R_2$ are cycloalkyl or cycloalkylalkyl, such groups preferably contain a total of 3–7 carbon atoms, with cyclopropyl, cyclopropylmethyl, cyclopentyl and cyclohexyl groups being preferred.

Examples of $R_1$ and/or $R_2$ which are aryl or aralkyl are phenyl and benzyl, which are preferred, and tolyl, xylyl, naphthyl, phenethyl and 3-phenylpropyl.

Preferred compounds of general Formula I are those wherein a. $R_2$ is methyl,
b. X is O, especially those of (a),
c. $R_4$ is H, especially those of (a) and (b),
d. $R_1$ is hydrocarbon of 1–18 carbon atoms, especially those of (a), (b) and (c).

Examples of $R_4$ groups, in addition to hydrogen, are lower alkyl of 1 to 4 carbon atoms, e.g., methyl and ethyl, aryl, e.g., phenyl, or hydrocarbon aryl as illustrated above for $R_1$ and $R_2$, lower acyl, preferably alkanoyl of 1–6 carbon atoms, e.g., acetyl, propionyl, butyryl and pivaloyl. Other examples of aryl are those as illustrated above for $R_1$ and $R_2$. When $R_4$ is acyl, the exact nature of the acylating group is not critical, since activity resides in the N-unsubstituted moiety. Thus, equivalents of the preferred lower-alkanoyl acylating groups are those of the formula RCO- wherein R is a hydrocarbon or substituted alkyl group as illustrated above for $R_1$ and $R_2$.

The racemic and optically active compounds of general Formula I are valuable neuropsychotropic medicinal agents. The novel compounds exhibit central-depressive, apomorphine-antagonistic and antinociceptive effects and thus exhibit a response spectrum similar to chlorpromazine (literature: Modern Problems of Pharmacopsychiatry, vol. 5, pp. 33–44: Janssen p. A. Y., "Chemical and Pharmacological Classification of Neuroleptics," edited by Bobon D. P. et al., S. Karger publishers, Basel-Munich-Paris-New York [1970]). On the other hand, the compounds of the present invention differ from chlorpromazine by a less pronounced reflex impairment, less pronounced sedative and narcotic properties, and by a different influence on the biogenous amines. Thus, for example, 4-(3,4-dimethoxyphenyl)-2-pyrrolidone has a barbital-sleep time prolonging effect which is about 20 times weaker than that of chlorpromazine.

The novel compounds are characterized by a rapid onset of effectiveness and a low order of acute toxicity.

The advantageous properties of the novel compounds is surprising because, as demonstrated in tests conducted in our laboratories, the corresponding p- and m-monosubstituted phenyl-2-pyrrolidones have, respectively, a different spectrum of activity or an only minor activity.

For example, 4-(4-chlorophenyl)-2-pyrrolidone, described in Japanese Pat. No. 70 16 692, has an anticonvulsive effect. The unsubstituted phenyl-2-pyrrolidones have only very weak activity.

The compounds of this invention can be used in the form of pharmaceutical compositions for the treatment of various neurological and psychic disorders, especially as neuroleptics having diminished extrapyramidal symptomatology, for example, schizophrenia and related psychotic states characterized by anxiety, hostility, agression, withdrawal, hallucination, thought-disturbances, delusion and agitation. The compounds of this invention are thus useful for the treatment of such disorders responding to chlorpromazine therapy.

The pharmaceutical compositions of this invention can be formulated using the vehicles customary for enteral or parenteral administration, such as, for example, water, alcohol, gelatin, gum arabic, lactose, amylose, magnesium stearate, talc, vegetable oils, polyalkylene glycol, etc. The preparations can be formulated in solid form, e.g., as tablets, capsules, dragees and suppositories, or in the liquid form, e.g., as solutions, suspensions and emulsions.

Although a single racemate or optical antipode of Formula I are generally employed in such compositions, mixtures thereof can also be employed, if desired.

For oral administration, the amount of active agent per oral dosage unit usually is 1-20 mg., preferably 5-10 mg. The daily dosage is usually 1-50 mg., preferably 10-30 mg. p.o. For parenteral application, the amount of active agent per dosage unit is usually 0.05 − 10 mg., preferably 0.1 − 5 mg. The daily dosage is usually 0.1 − 20 mg., preferably 0.2 − 5 mg. i.v. or i.m.

The novel 4-(polyalkoxyphenyl)-2-pyrrolidones of general Formula I can be produced by means of conventional reactions wherein a. 4-(substituted phenyl)-2-pyrrolidone-3-carboxylic acid alkyl esters of general Formula II

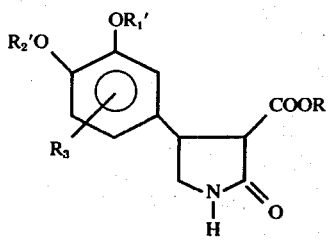

wherein $R_1'$ and $R_2'$ are $R_1$ and $R_2$, respectively, or hydrogen, $R_3$ has the values given above and R is acyl, preferably lower acyl, are saponified and decarboxylated; or b. 3-(substituted phenyl)-4-aminobutyric acid alkyl esters of general Formula III

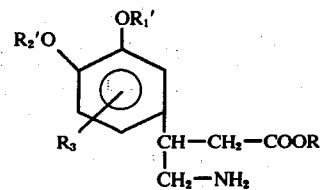

wherein $R_1'$, $R_2'$, $R_3$ and R have the values given above or an acid addition salt thereof, are cyclized with splitting off of an ROH alcohol; or c. 3-(substituted phenyl)-4-aminobutyric acid of the general Formula IV

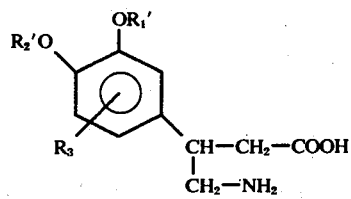

wherein $R_1'$, $R_2'$ and $R_3$ have the values given above or an acid addition salt thereof, is cyclized with splitting off of water; and optionally, in the compounds obtained according to (a), (b) or (c) a free hydroxy group ($OR_1'$ or $OR_2'$) is alkylated or arylated, and/or a free imino group (NH) is alkylated, arylated or acylated, and/or the carbonyl oxygen is exchanged with sulfur; and/or a racemate is subjected to a racemate splitting step and one or both optically active antipodes thereof are isolated.

Conventional methods are employed for the preparation of the compounds according to general Formula I.

The saponification according to method (a) is accomplished with aqueous alkali, suitably in a water-miscible solvent, e.g., in an alcohol, such as ethanol, in tetrahydrofuran, or in dioxane at temperatures of between approximately 60° and 150° C., preferably at the boiling temperature. The decarboxylation according to (a) takes place by heating the carboxylic acid to about 160°–280° C. Preferably, the compound is heated under vacuum. The $CO_2$ can also be split off optionally in the presence of a high-boiling inert solvent, e.g., diphenyl ether or quinoline.

The cyclization according to method (b) is effected, while splitting off alcohol, in an organic solvent such as, for example, dimethylformamide, dimethylacetamide, tetrahydrofuran, dioxane, benzene, toluene, xylene, etc., while heating the reaction mixture to about 50°–150° C. When starting with a salt, e.g., the hydrochloride, of the amino acid ester of general Formula III, the mixture is heated in the presence of a tertiary base. Suitable tertiary bases are trialkylamines, for example, triethylamine and tributylamine, as well as, for example, N-methylmorpholine, diethylcyclohexylamine, pyridine, etc.

According to method (c), the cyclization is conducted while splitting off water at temperatures of between about 160° and 280° C. It is advantageous to work under a vacuum so that the split-off water can be more easily removed and the access of atmospheric oxygen is prevented. When starting with the corresponding acid addition salts, the reaction is carried out, as under (b), by heating in the presence of a tertiary base.

The compounds obtained according to (a), (b), or (c) wherein $R_1'$ or $R_2'$ is a hydrogen atom must subsequently be converted into the final products of general Formula I by O-alkylation. The alkylation is preferably conducted in a conventional manner with the corresponding $R_1$- and/or $R_2$- halogenide or -tosylate. Suitable halogenides are the chlorides, bromides, and iodides. For purposes of the alkylation, the hydroxy compound is, for example, dissolved in a polar solvent and heated to temperatures of between 30° and 150° C. in the presence of a base together with the alkylating agent. Examples of bases are sodium hydride, potassium carbonate, alkali alcoholates, such as sodium ethylate, potassium butylate, and potassium tert.-butylate, of polar solvents, dimethylformamide, dimethylacetamide, tetrahydrofuran, dioxane, ketones, such as acetone and methyl isobutyl ketone, as well as alcohols, such as ethanol, butanol, and tert.-butanol.

The alkylation, arylation, or acylation of the imino group likewise take place according to conventional methods. Thus, the imino compound ($R_4 = H$) is dissolved in a polar solvent and heated to about 40°–150° C. in the presence of a salt-forming agent with an alkyl, aryl, or acyl halogenide. Suitable polar solvents are dimethylformamide, dimethylacetamide, tetrahydrofuran, dioxane, ketones such as acetone and methyl isobutyl ketone, as well as alcohols, such as ethanol and butanol. Suitable salt-forming agents are, for example, sodium hydride, potassium carbonate, alkali alcoholates, such as sodium ethylate, potassium tert.-butylate, etc. The reaction with a haloaryl, e.g., iodobenzene, can also be effected without a solvent, preferably in the presence of pulverized copper.

The exchange of the carbonyl oxygen against sulfur is conducted in the same way as described in the literature for such compounds. (Compare, in this connection, J. W. Scheeren, P. H. J. Ohms, R. J. F. Nivard, Synthesis 1973, 149–151.) Suitable for this purpose is, for example, a polysulfide, such as phosphorus pentasulfide, in a solvent or solvent mixture in the presence of a base. The reaction can also be effected in a suspension. Suitable solvents or suspension agents are, for instance, acetonitrile, tetrahydrofuran, diethyl ether, glycol dimethyl ether. Advantageous bases are sodium bicarbonate, potassium carbonate, etc. The reaction is terminated, at 30°–120° C., after 3–24 hours.

The starting compounds of Formulae II, III, and IV can likewise be prepared according to known methods, for example in the following ways:

Starting with the benzaldehyde substituted by $R_1'$, $R_2'$, $R_3$ the corresponding benzal-malonic acid dialkyl ester is produced with the dialkyl ester of malonic acid. The substituted benzal-malonic acid dialkyl ester can be converted with nitromethane in the presence of tetramethylguanidine, by way of the 1-(substituted phenyl)-2-nitroethylmalonic acid dialkyl ester and subsequent pressurized hydrogenation with the use of Raney nickel, into 4-(substituted phenyl)-2-pyrrolidone-3-carboxylic acid alkyl esters of the general Formula II.

To produce 3-(substituted phenyl)-4-aminobutyric acid alkyl esters of general Formula III, HCN is added to the double bond of the benzal-malonic acid diester with potassium cyanide in aqueous alcohol under heating to 60° C., with the simultaneous splitting off of a carbalkoxy group; and the cyano compound is hydrogenated under pressure in the presence of platinum dioxide. If the addition of HCN is conducted under boiling heat, the corresponding butyric acid of general Formula IV is obtained.

The reactions of the substituted benzaldehyde to obtain the compounds of Formulae II, III, and IV will be explained once more with reference to the following reaction scheme:

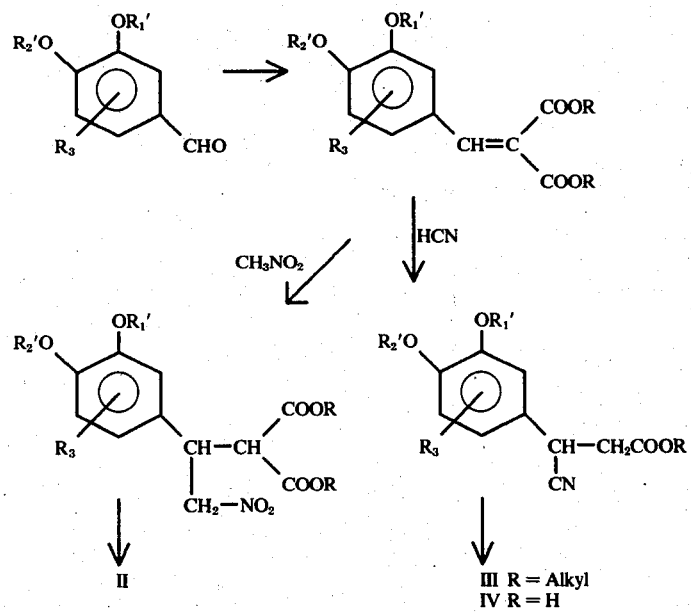

The processes will be described in greater detail below.

The term "worked up as usual" means extraction with the indicated solvent, washing of the organic phase with saturated NaCl solution, drying over anhydrous calcium sulfate, and evaporation under vacuum at a bath temperature of 40°–45° C. Specific mention is made of any additional treatment of the organic base, such as washing with acid or an alkali.

The indicated yields are not optimum values. No attempts at optimization have been made.

The temperatures are indicated in degrees Celsius (° C.).

The compounds set forth as starting materials were tested for sufficient purity by thin-layer chromatography in at least two systems and with the aid of IR spectra. All other substances are analytically pure (C, H, N determinations; IR, UV, and NMR spectra; thin-layer chromatography; partially titrations and gas chromatography).

Adjacent the melting point, determined on the Kofler heating bench, the solvents used for the recrystallization are indicated in parentheses.

The following abbreviations are employed for solvents:

| | |
|---|---|
| DMF | dimethylformamide |
| EE | ethyl acetate |
| DIP | diisopropyl ether |
| W | water |
| AcOH | glacial acetic acid |
| Bz | benzene |

The compounds of general Formula II can be prepared, for example, as follows:

A. Benzal-Malonic Acid Diethyl Ester

One mole of a correspondingly substituted benzaldehyde is heated on a water trap with 160 g. (1 mole) of diethyl malonate, 30 ml. of glacial acetic acid, and 3 ml. of piperidine in 1 liter of benzene until 1 mole of water has been split off. The benzenic solution is worked up as usual.

3-Isobutoxy-4-methoxybenzaldehyde, not heretofore described in the literature, is prepared as follows:

108 g. of 3-hydroxy-4-methoxybenzaldehyde (710 millimoles) is heated for 26 hours to the boiling point with 40.5 g. of potassium hydroxide (723 mmol) and 120 g. of isobutyl bromide (875 mmol) in 250 ml. of ethanol under agitation. After the alcohol has been distilled off under vacuum, the residue is worked up as usual with ethyl acetate, but washed additionally with 2N sodium hydroxide solution. By acidification, 35 g. of starting material is recovered from the alkaline extract. The yield of 3-isobutoxy-4-methoxybenzaldehyde is 80 g.; m.p. 70° (heptane).

In the following table, the yields as well as the boiling and melting points of several compounds have been compiled:

(A) 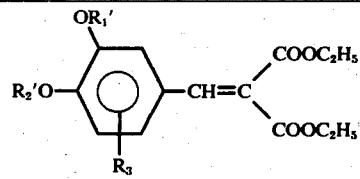

| | $R_1'$ | $R_2'$ | $R_3$ | Yield (% of Theory) | Boiling pt. Melting pt. (Recrystallization Agent) |
|---|---|---|---|---|---|
| a | —$CH_3$ | —$CH_3$ | —H | 70 | b.p.$_{0.6}$ 185–189° |
| b | —$CH_2$— | | —H | 53 | b.p.$_{0.4}$172° |
| c | —$CH_2CH_2$— | | —H | 88 | b.p.$_1$ 227–289° |
| d | —$CH_2CH(CH_3)_2$— | —$CH_3$ | —H | 95 | b.p.$_{0.1}$ 190–192° |
| e | —H | —$CH_3$ | —H | 78 | b.p.$_1$ 213–215° m.p. 86° (DIP) |
| f | —$CH_3$ | —H | —H | 77 | m.p. 121° (DIP) |
| g | —$CH_3$ | —$CH_3$ | 2-$OCH_3$ | 100 | crude product (TLC, IR) |
| h | —$CH_3$ | —$CH_3$ | 5-$OCH_3$ | 75 | b.p.$_{0.2}$ 180–182° m.p. ~ 70° |
| i | —$CH_3$ | —$CH_3$ | 6-$OCH_3$ | 90 | m.p. 100° (DIP) |

B. 1-(Substituted Phenyl)-2-nitroethylmalonic Acid Diethyl Ester 500 millimoles of the corresponding benzal-malonic acid diethyl ester (see [A]) is dissolved in 250 ml. of nitromethane and combined with 12.7 ml. of tetramethylguanidine under agitation at 0°. After the exothermic reaction has faded, the mixture is further stirred at room temperature for 18 hours. Then, the mixture is worked up as usual with ethyl acetate, but additionally washed with 2N hydrochloric acid. The acetoxymethoxybenzal-malonic esters required for Examples B(b) and B(c) are produced as follows:

150 g. of (3-hydroxy-4-methoxybenzal)-malonic acid diethyl ester (510 mmol) (see A[e]) is dissolved in 450 ml. of pyridine and, under ice cooling, 57 ml. of acetic anhydride (604 mmol) is added thereto dropwise. After allowing the reaction mixture to stand for 18 hours at room temperature, the pyridine is withdrawn under vacuum. The mixture is worked up as usual with ethyl acetate, yielding 163 g. of (3-acetoxy-4-methoxybenzal)-malonic acid diethyl ester (95% of theory); m.p. 75°–77° (diisopropyl ether).

Analogously, the (4-hydroxy-3-methoxybenzal)-malonate (see A[f]) is acetylated to the corresponding 4-acetoxy-3-methoxy compound. Yield: 95% M.p. 51° (diisopropyl ether petroleum ether).

(B) 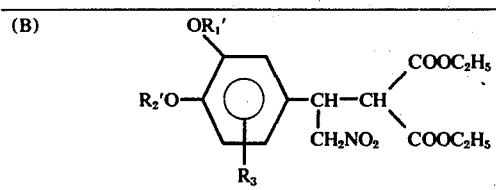

| | $R_1'$ | $R_2'$ | $R_3$ | Yield (% of Theory) | Melting point (Recrystallizing Agent) |
|---|---|---|---|---|---|
| a | —CH₃ | —CH₃ | —H | 59 | 75° (methylene chloride-DIP) |
| b | —COCH₃ | —CH₃ | —H | 95 | crude product (TLC, IR) |
| c | —CH₃ | —COCH₃ | —H | 95 | Crude product (TLC, IR) |
| d | —CH₃ | —CH₃ | 2-OCH₃ | 65 | chromatography on SiO₂ (cyclohexane-ethyl acetate 1 : 1) |
| e | —CH₃ | —CH₃ | 6-OCH₃ | 70 | chromatography on SiO₂ (cyclohexane-ethyl acetate 1 : 1) |

C. 4-(Substituted Phenyl)-2-pyrrolidone-3-carboxylic Acid Ethyl Ester (II)

300 millimoles of the corresponding 1-phenyl-2-nitroethylmalonic acid diethyl ester is dissolved in 700 ml. of methanol and hydrogenated with about 10 g. of Raney nickel at 60° and under a pressure of 95 atmospheres until 3 moles of hydrogen have been absorbed. Thereafter, the product is filtered off from the catalyst, concentrated under vacuum, and the oily residue is recrystallized.

(C) 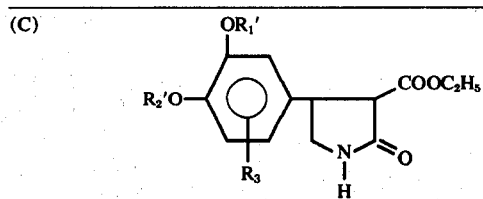

| | $R_1'$ | $R_2'$ | $R_3$ | Yield (% of Theory) | Melting point (Recrystallizing Agent) |
|---|---|---|---|---|---|
| a | —CH₃ | —CH₃ | —H | 84 | 106° (EE) |
| b | —H | —CH₃ | —H | 70 | 125° (EE-DIP) (splitting off the acetyl group during hydrogenation, and working-up step) |
| c | —CH₃ | —COCH₃ | —H | 62 | 172° (EE) |
| d | —CH₃ | —CH₃ | 2-OCH₃ | 60 | 99° (EE-DIP) |
| e | —CH₃ | —CH₃ | 6-OCH₃ | 20 | 131° (ethanol) |

The compounds of general Formula III can be produced, for example, as follows:

D. 3-(Substituted Phenyl)-3-cyanopropionic Acid Ethyl Ester 100 millimoles of a corresponding benzal-malonic ester (see [A]) is combined, in 180 ml. of ethanol, with a solution of 6.5 g. of potassium cyanide (100 mmol) in 25 ml. of water and heated for 7 hours to 60°. After allowing the mixture to stand for 18 hours at room temperature, the solvents are removed under vacuum, and the residue is worked up as usual with ethyl acetate, including an extraction with 1N sodium hydroxide solution. If desired, the corresponding 3-phenyl-3-cyanopropionic acid ethyl esters can be obtained by acidification from the sodium hydroxide solution extract.

(D) 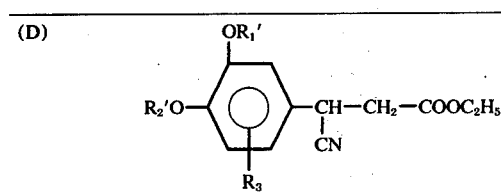

| | $R_1'$ | $R_2'$ | $R_3$ | Yield (% of Theory) | Boiling pt. Melting pt. (Recrystallizing Agent) |
|---|---|---|---|---|---|
| a | —CH₃ | —CH₃ | —H | 85 | b.p.₀.₁ 177–182° |
| b | —CH₂— | | —H | 82 | crude product (TLC, IR) |
| c | —CH₂CH₂— | | —H | 84 | crude product (TLC, IR) |
| d | —CH₂CH(CH₃)₂ —CH₃ | | —H | 83 | crude product (TLC, IR) |
| e | —CH₃ | —H | —H | 91 | crude product (TLC, IR) |
| f | —CH₃ | —CH₃ | 5-OCH₃ | 60 | m.p. 84° (EtOH) |

E. 3-(Substituted Phenyl)-4-aminobutyric Acid Ethyl Ester Hydrochloride (III)

50 millimoles of a 3-phenyl-3-cyanopropionic acid ethyl ester is hydrogenated in 60 ml. of glacial acetic acid over 1 g. of platinum oxide at room temperature and 100 atmospheres until 2 moles of hydrogen have been absorbed. The reaction product is filtered off from the catalyst under vacuum and, after adding 25 ml. of 2N methanolic hydrochloric acid, evaporated under vacuum to a small volume.

(E) 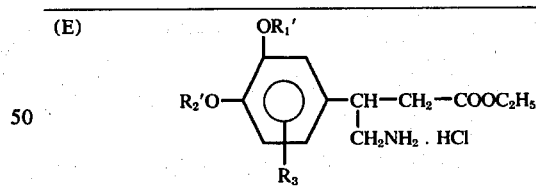

| | $R_1'$ | $R_2'$ | $R_3$ | Yield (% of Theory) | Melting pt. (Recrystallizing Agent) |
|---|---|---|---|---|---|
| a | —CH₃ | —CH₃ | —H | 90 | m.p. 185° (AcOH) |
| b | —CH₂— | | —H | 79 | crude product (TLC, IR) |
| c | —CH₂CH₂— | | —H | 100 | crude product (TLC, IR) |
| d | —CH₂CH(CH₃)₂ —CH₃ | | —H | 63 | m.p. 124° (EE) |
| f | —CH₃ | —CH₃ | 5-OCH₃ | 100 | crude product (TLC, IR) |
| g | —CH₃ | —H | —H | 100 | crude product (TLC, IR) |

The compounds of general Formula IV can be prepared as follows:

F. 3-(Substituted Phenyl)-3-cyanopropionic Acid

By reaction a corresponding substituted benzalmalonic ester (see under [A]) with potassium cyanide in the same quantitative ratios and with the same reaction times as described under (D), but under boiling heat, the 3-(substituted phenyl)-3-cyanopropionic acids are obtained. These acids are isolated after evaporation of the solvents, taking up the residue in water, washing with ethyl acetate, and acidification of the aqueous phase; the products are purified by crystallization.

(F)

$$R_2'O-\underset{R_3}{\underset{|}{\bigcirc}}-OR_1' \quad \underset{CN}{\overset{|}{CH}}-CH_2-COOH$$

| | $R_1'$ | $R_2'$ | $R_3$ | Yield (% of Theory) | Melting pt. (Recrystallizing Agent) |
|---|---|---|---|---|---|
| a | —CH₃ | —CH₃ | —H | 54 | m.p. 133–135° (ethanol) |
| b | —CH₂— | | —H | 63 | crude product (TLC, IR) |
| c | —CH₂CH₂— | | —H | 76 | crude product (TLC, IR) |
| d | —CH₃ | —CH₃ | 5-OCH₃ | 78 | crude product (TLC, IR) |

G. 3-(Substituted Phenyl)-4-aminobutyric Acid Hydrochloride (IV)

100 millimoles of 3-(substituted phenyl)-3-cyanopropionic acid (see [F]) is hydrogenated in 200 ml. of glacial acetic acid with the addition of 9.5 ml. of concentrated hydrochloric acid over 3 g. of platinum dioxide at room temperature and 100 atmospheres until 2 moles of hydrogen have been absorbed. The product is filtered off from the catalyst and concentrated under vacuum. The 3-(substituted phenyl)-4-aminobutyric acid hydrochlorides are obtained by crystallization of the mostly oily residue.

(G)

$$R_2'O-\underset{R_3}{\underset{|}{\bigcirc}}-OR_1' \quad \underset{CH_2-NH_2 \cdot HCl}{\overset{|}{CH}}-CH_2-COOH$$

| | $R_1'$ | $R_2'$ | $R_3$ | Yield (% of Theory) | Melting pt. (Recrystallizing Agent) |
|---|---|---|---|---|---|
| a | —CH₃ | —CH₃ | —H | 50 | m.p. 220° (decomp.) (AcOH) |
| b | —CH₂— | | —H | 43 | m.p. 210° (1N HCl) |
| c | —CH₂CH₂— | | —H | 52 | m.p. 207 (ethanol-DIP) |
| d | —CH₃ | —CH₃ | 5-OCH₃ | 45 | m.p. 204° (isopropanol) |

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

4-(Substituted Phenyl)-2-pyrrolidones

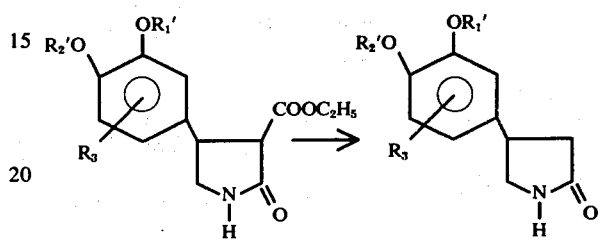

50 millimoles of a 4-(substituted phenyl)-2-pyrrolidone-3-carboxylic acid ethyl ester (according to [C]) is heated to the boiling point for 1 hour with 200 ml. of ethanol and 60 ml. of 1N sodium hydroxide solution. After the solvents have been distilled off under vacuum, the residue is taken up in ethyl acetate and extracted with water, optionally while adding some sodium hydroxide solution. After saturation with NaCl, 4-(substituted phenyl)-2-pyrrolidone-3-carboxylic acid is precipitated from the aqueous phase with 5N hydrochloric acid. After allowing the reaction mixture to stand for a certain time under cold conditions, the reaction mixture is vacuum-filtered and washed with a small amount of ice water. Decarboxylation of the pyrrolidon-carboxylic acid takes place by heating to 200° under vacuum until the evolution of $CO_2$ has ceased. The residue is recrystallized, optionally while adding carbon.

| | $R_1'$ | $R_2'$ | $R_3$ | Yield (% of Theory) | Boiling pt. Melting pt. (Recrystallizing Agent) |
|---|---|---|---|---|---|
| a | —CH₃ | —CH₃ | —H | 81 | 120° (W) |
| b | —H | —CH₃ | —H | 45 | 144° (isopropanol) |
| c | —CH₃ | —H | —H | 40 | b.p.₀.₆ 230° (*) |
| d | —CH₃ | —CH₃ | 2-OCH₃ | 57 | 93° (EE) |
| e | —CH₃ | —CH₃ | 6-OCH₃ | 65 | 103° (EE) |

(*)Chromatography on silica gel (Bz. AcOH—H₂O, 10:10:1) under simultaneous saponification of the 4-acetoxy group.

1(a) 4-(3,4-dimethoxyphenyl)-2-pyrrolidone
1(b) 4-(3-hydroxy-4-methoxyphenyl)-2-pyrrolidone
1(c) 4-(4-hydroxy-3-methoxyphenyl)-2-pyrrolidone
1(d) 4-(2,3,4-trimethoxyphenyl)-2-pyrrolidone
1(e) 4-(3,4,6-trimethoxyphenyl)-2-pyrrolidone

EXAMPLE 2

4-(Substituted Phenyl)-2-pyrrolidones

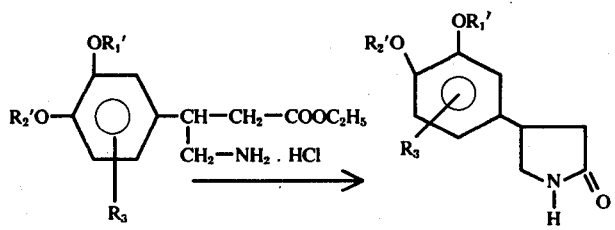

Method I 10 millimoles of a 3-(substituted phenyl)-4-aminobutyric acid ethyl ester hydrochloride is dissolved in 15 ml. of dimethylformamide, combined with 1.4 ml. of triethylamine (10 mmol), and heated for 6 hours to 70°. After evaporation under vacuum, the mixture is worked up as usual with ethyl acetate.

Method II

Under agitation, 10 mmol of a 3-(substituted phenyl)-4-aminobutyric acid ethyl ester hydrochloride and 1.4 ml. of triethylamine (10 mmol) are heated in 50 ml. of benzene to the boiling point until the ninhydrin reaction is negative; the mixture is then worked up as usual.

| | Method | $R_1'$ | $R_2'$ | $R_3$ | Yield (% of Theory) | Boiling pt. Melting pt. (Recrystallizing Agent) |
|---|---|---|---|---|---|---|
| a | I | —$CH_3$ | —$CH_3$ | —H | 63 | m.p. 120° (W) |
| b | II | —$CH_2$— | | —H | 49 | m.p. 157° (EE) |
| c | II | —$CH_2CH_2$— | | —H | 54 | m.p. 104° (EE) |
| d | II | —$CH_2CH(CH_3)_2$ | | —H | 50 | m.p. 150° (EE) |
| e | I | —$CH_3$ | $CH_3$—H | —H | 10 | b.p.$_{0.6}$ 230° chromatography on $SiO_2$ (Bz—AcOH—$H_2O$, 10:10:1) |
| f | II | —$CH_3$ | —$CH_3$ | 5-$OCH_3$ | 72 | m.p. 129° (W) |

2(a) 4-(3,4-dimethoxyphenyl)-2-pyrrolidone
2(b) 4-(3,4-methylenedioxyphenyl)-2-pyrrolidone
2(c) 4-(3,4-ethylenedioxyphenyl)-2-pyrrolidone
2(d) 4-(3-isobutoxy-4-methoxyphenyl)-2-pyrrolidone
2(e) 4-(4-hydroxy-3-methoxyphenyl)-2-pyrrolidone
2(f) 4-(3,4,5-trimethoxyphenyl)-2-pyrrolidone

EXAMPLE 3

4-(3,4-Dimethoxyphenyl)-2-pyrrolidone

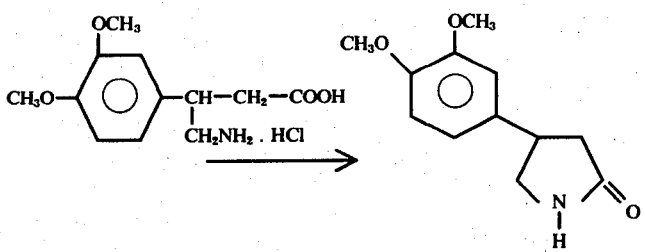

2.76 g. of 4-amino-3-(3,4-dimethoxyphenyl)-butyric acid hydrochloride is combined with 1.4 ml. of triethylamine (10 mmol) in 2 ml. of ethanol and then heated under vacuum (0.4 – 0.6 torr [mm. Hg]) to 200°–210° until no free amino acid can be detected any longer by a spot analysis with ninhydrin. The usual working up procedure with ethyl acetate yields, from the residue, 1.26 g. of 4-(3,4-dimethoxyphenyl)-2-pyrrolidone (57% of theory); m.p. 120° (water).

EXAMPLE 4

4-(Alkoxymethoxyphenyl)-2-pyrrolidones

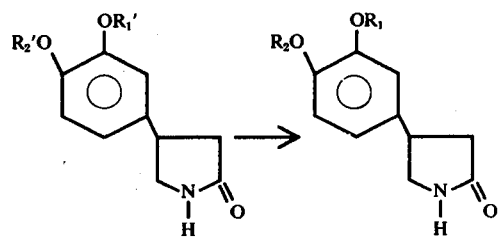

Method A 10 millimoles of a 4-(hydroxyalkoxyphenyl)-2-pyrrolidone is dissolved in 5 ml. of dimethylformamide, combined under ice cooling with 500 g. of a 50% sodium hydride — paraffin oil suspension (10.5 mmol), and heated gradually to 60° under agitation. After the evolution of hydrogen has ceased, 11 mmol of the corresponding R-halogenide and 100 mg. of sodium iodide in 3 ml. of dimethylformamide are added thereto at 0°, and the mixture is heated for 3 hours to 100° under agitation. Then, the solvent is distilled off under vacuum and the residue worked up as usual with ethyl acetate, including an extraction with 2N sodium hydroxide solution.

Method B 10 millimoles of a 4-(hydroxyalkoxyphenyl)-2-pyrrolidone, 11 mmol of the corresponding halogenide, and 1.45 g. of potassium carbonate (10.5 mmol) are heated in 30 ml. of acetone for 38 hours under agitation to the boiling point. The residue remaining after the inorganic salts have been vacuum-filtered and the residue evaporated under vacuum is worked up as indicated in method A.

Method C 10 millimoles of a 4-(hydroxyalkoxyphenyl)-2-pyrrolidone is dissolved in 22 ml. of 0.5N sodium butylate solution in butanol and heated to the boiling point with 11 mmol of the corresponding halogenide for 10 hours under agitation. The reaction mixture is worked up as described under method A.

| $R_2=CH_3$ | $R_1$ | Method | Yield (% of Theory) | Melting Point (Recrystallizing Agent) |
|---|---|---|---|---|
| a | $-C_2H_5$ | C | 62 | 123° (EE) |
| b | $-C_3H_7$ | B | 42 | 124° (EE-DIP) |
| c | $-C_4H_9$ | C | 47 | 125° (DIP) |
| d | $-C_6H_{13}$ | A | 48 | 119° (EE-DIP) |
| e | $-CH(CH_3)_2$ | A | 44 | 123° (EE-DIP) |
| f | $-CH(CH_3)(C_2H_5)$ | B | 41 | 105° (EE-DIP) |
| g | $-CH_2-CH(CH_3)_2$ | B | 40 | 150° (EE) |
| h | $-CH_2-CH=CH_2$ | B | 46 | 104° (EE-DIP) |
| i | $-CH_2-CH=C(CH_3)_2$ | B | 38 | 123° (EE-DIP) |
| k | $-CH_2OCH_3$ | A | 38 | 94° (triturate with DIP) |
| l | $-CH_2-CON(C_2H_5)_2$ | A | 56 | 117° (EE-petroleum ether) |
| m | $-CH_2CH_2OH$ | A | 34 | 108° (EE) |
| n | $-CH_2CF_3$ | B | 36 | 110° (EE) |
| o | $-CH_2-C_6H_5$ | A | 57 | 132° (EE) |
| p | $-C_6H_5$ | $K_2CO_3$, $I-C_6H_5$ DMF 30' 130° | 71 | 132° (EE) |
| a' | $-C_{10}H_{21}$ | A | 49 | 117° (EE) |
| b' | $-C_{18}H_{37}$ | A | 40 | 119° (EE) |
| c' | $-CH_2-CH(CH_3)(C_2H_5)$ | A | 50 | 140° (EE) |
| d' | $-CH_2-C(CH_3)_3$ | A | 21 | 166° (EE-DIP) |
| e' | $-CH_2-CH_2-CH(CH_3)_2$ | A | 61 | 139° (EE) |
| f' | $-CH_2-C\equiv CH$ | A * | 60 | 116° (EE-DIP) |

-continued

| $R_2=CH_3$ | $R_1$ | Method | Yield (% of Theory) | Melting Point (Recrystallizing Agent) |
|---|---|---|---|---|
| g' | —CH$_2$—C≡N | A | 48 | 144° (EE-DIP) |
| h' | cyclopropyl | A | 20 | 140° (EE-DIP) |
| i' | cyclobutyl | A * | 30 | 132° (EE) |
| k' | cyclopentyl | A | 20 | 128° (EE-DIP) |
| l' | 2-methylcyclobutyl | A ** | 22 | 128° (EE-DIP) |
| m' | 1-methylcyclobutyl | A ** | 19 | 120° (EE-DIP) |
| n' | tetrahydrothienyl | A ** | 12 | 128° *** |
| o' | tetrahydrofuryl | A ** | 20 | 107° *** |
| p' | —CH$_2$—cyclopropyl | A | 50 | 123° (EE) |
| q' | —CH$_2$—cyclobutyl | A ** | 36 | 132° (EE-Hexane) |
| r' | 2-oxacyclopentyl | A | 32 | 173–176° (Ethanol) |
| s' | —CH$_2$—C(=CH$_2$)CH$_3$ | B | 63 | 130°(EE-DIP) |

* Using hexamethylphosphoric triamide instead of DMF
** The tosylate was used instead of the R-halogenide
*** Chromatography on SiO$_2$, CH$_2$Cl$_2$-acetone (1:1)

| $R_1=CH_3$ | $R_2$ | Method | Yield (% of Theory) | Melt. Pt. (Recryst. Agent) |
|---|---|---|---|---|
| q | —C$_2$H$_5$ | C | 47 | 168° (EE) |
| r | —C$_4$H$_9$ | C | 62 | 118° (DIP) |
| s | —CH$_2$—CON(C$_2$H$_5$)$_2$ | A | 53 | 95° (EE) |
| t' | —CH$_2$—C≡CH | A(*) | 61 | 126° (EE) |
| u' | cyclobutyl | A(*) | 62 | 104° (EE) |

| $R_1=R_2$ | $R_2$ | Method | Yield (% of Theory) | Melt.Pt. (Recryst. Agent) |
|---|---|---|---|---|
| v' | —C$_2$H$_5$ | A(+) | 83 | 146–148° (EE-DIP) |
| w' | —CH$_2$—CH(CH$_3$)CH$_3$ | A(+) | 42 | 88° (hexane) |

(*) Using hexamethylphosphoric triamide instead of DMF.
(+) Method A, but using 4-(3,4-dihydroxyphenyl)-2-pyrrolidone as the starting material 4 a 4-(3-ethoxy-4-methoxyphenyl)-2-pyrrolidone
b 4-(3-propoxy-4-methoxyphenyl)-2-pyrrolidone
c 4-(3-butoxy-4-methoxyphenyl)-2-pyrrolidone
d 4-(3-hexyloxy-4-methoxyphenyl)-2-pyrrolidone
e 4-(3-isopropoxy-4-methoxyphenyl)-2-pyrrolidone -continued f 4-(3-[1-methylpropoxy]-4-methoxyphenyl)-2-pyrrolidone
g 4-(3-isobutoxy-4-methoxyphenyl)-2-pyrrolidone
h 4-(3-allyloxy-4-methoxyphenyl)-2-pyrrolidone
i 4-(3-[3-methyl-2-butenyloxy]-4-methoxyphenyl)-2-pyrrolidone
k 4-(3-methoxymethoxy-4-methoxyphenyl)-2-pyrrolidone
l 4-(3-diethylaminocarbonylmethoxy-4-methoxyphenyl)-2-pyrrolidone
m 4-(3-[2-hydroxyethoxy]-4-methoxyphenyl)-2-pyrrolidone
n 4-(3-[2,2,2-trifluoroethoxy]-4-methoxyphenyl)-2-pyrrolidone
o 4-(3-benzyloxy-4-methoxyphenyl)-2-pyrrolidone
p 4-(3-phenoxy-4-methoxyphenyl)-2-pyrrolidone
q 4-(3-methoxy-4-ethoxyphenyl)-2-pyrrolidone
r 4-(3-methoxy-4-butoxyphenyl)-2-pyrrolidone
s 4-(3-methoxy-4-diethylaminocarbonylmethoxyphenyl)-2-pyrrolidone
a' 4-(3-decyloxy-4-methoxyphenyl)-2-pyrrolidone
b' 4-(3-octadecyloxy-4-methoxyphenyl)-2-pyrrolidone
c' 4-(3-[2-methylbutyl]-oxy-4-methoxyphenyl)-2-pyrrolidone
d' 4-(3-neopentyloxy-4-methoxyphenyl)-2-pyrrolidone
e' 4-(3-isopentyloxy-4-methoxyphenyl)-2-pyrrolidone
f' 4-(3-[2-propinyl]-oxy-4-methoxyphenyl)-2-pyrrolidone
g' 4-(3-cyanomethyloxy-4-methoxyphenyl)-2-pyrrolidone
h' 4-(3-cyclobutoxy-4-methoxyphenyl)-2-pyrrolidone
i' 4-(3-cyclopentyloxy-4-methoxyphenyl)-2-pyrrolidone
k' 4-(3-cyclohexyloxy-4-methoxyphenyl)-2-pyrrolidone
l' 4-(3-[3-methylcyclopentyl]-oxy-4-methoxyphenyl)-2-pyrrolidone
m' 4-(3-[2-methylcyclopentyl]-oxy-4-methoxyphenyl)-2-pyrrolidone
n' 4-(3-[3-tetrahydrothienyl]-4-methoxyphenyl)-2-pyrrolidone
o' 4-(3-[3-tetrahydrofuryl]-oxy-4-methoxyphenyl)-2-pyrrolidone
p' 4-(3-cyclopropylmethyloxy-4-methoxyphenol)-2-pyrrolidone
q' 4-(3-cyclopentylmethyloxy-4-methoxyphenyl)-2-pyrrolidone
r' 4-(3-[2-oxacyclopentyl]-4-methoxyphenyl)-2-pyrrolidone
s' 4-(3-methallyloxy-4-methoxyphenyl)-2-pyrrolidone
t' 4-(4-propinyloxy-3-methoxyphenyl)-2-pyrrolidone
u' 4-(4-cyclopentyloxy-3-methoxyphenyl)-2-pyrrolidone
v' 4-(3,4-diethoxyphenyl)-2-pyrrolidone
w' 4-(3,4-diisobutoxyphenyl)-2-pyrrolidone.

The starting material for producing the compounds 4 v' and 4 w' (4-[3,4-dihydroxyphenyl]-2-pyrrolidone) is prepared from the dimethyl ether 1 a as follows:

4.75 g. of 4-(3,4-dimethoxyphenyl)-2-pyrrolidone (20 mmol) is dissolved in 130 ml. of methylene chloride and at −80° combined dropwise under the exclusion of moisture and under agitation with 11.0 g. of boron tribromide (44 mmol), dissolved in 40 ml. of methylene chloride. The mixture is allowed to warm up to room temperature overnight, poured into water, and the crystalline precipitate is vacuum-filtered. The aqueous phase is extracted with ethyl acetate after saturation with NaCl. The ethyl acetate extract is concentrated by evaporation, and the residue is recrystallized from water together with the crystalline precipitate, thus obtaining 3.35 g. of 4-(3,4-dihydroxyphenyl)-2-pyrrolidone, m.p. 209°–215°.

EXAMPLE 5
1-Substituted
4-(3,4-Dimethoxyphenyl)-2-pyrrolidones

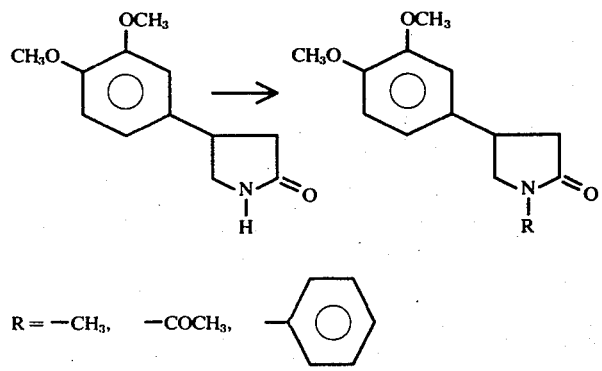

a. 4-(3,4-Dimethoxyphenyl)- 1-methyl-2-pyrrolidone 2.21 g. of 4-(3,4-dimethoxyphenyl)-2-pyrrolidone (10 mmol) is dissolved in 15 ml. of dimethylformamide, combined under ice cooling with 530 mg. of a 50% sodium hydride — paraffin suspension (11 mmol), and gradually heated to 60° under agitation. After the evolution of hydrogen has ceased, 1.56 g. of methyl iodide (11 mmol) in 5 ml. of dimethylformamide is added dropwise at 0° and the mixture heated for 15 minutes to 50°. Thereafter, the mixture is poured into water, worked up as usual with ethyl acetate, and the product thus obtained is 1.3 g. of 4-(3,4-dimethyoxyphenyl)-1-methyl-2-pyrrolidone (55% of theory); m.p. 69° (diisopropyl ether).

b. 1-Acetyl-4-(3,4-dimethoxyphenyl)-2-pyrrolidone

With the use of 0.86 g. of acetyl chloride (11 mmol) in place of the methyl iodide, 1-acetyl-4-(3,4-dimethoxyphenyl)-2-pyrrolidone is obtained analogously to method (a). Yield: 1.4 g. (53% of theory); m.p. 135° (ethanol).

c. 4-(3,4-Dimethoxyphenyl)-1-phenyl-2-pyrrolidone 2.21 g. of 4-(3,4-dimethoxyphenyl)-2-pyrrolidone (10 mmol), 3.5 g. of iodobenzene (17 mmol), 1.44 g. of potassium carbonate (10.4 mmol), and 100 mg. of pulverized copper are heated for 2 hours to 180°. The mixture is worked up as usual with ethyl acetate, yielding 2.2 g. of 4-(3,4-dimethoxyphenyl)-1-phenyl-2-pyrrolidone (74% of theory); m.p. 104° (ethyl acetate/diisopropyl ether).

d. 4-(3,4-Dimethoxyphenyl)-2-pyrrolidone-1-acetamide

Analogously to 5(a), but with 5 ml. of hexamethylphosphoric triamide as the solvent, the sodium salt of 4-(3,4-dimethoxyphenyl)-2-pyrrolidone is prepared; this product is combined with 0.94 g. of chloroacetamide (10 mmol) at 0°. The reaction mixture is heated for 4 hours to 70°–90°, cooled, diluted with water, and worked up as usual with ethyl acetate, including an extraction with 2N sodium hydroxide solution. Yield: 0.64 g. (23% of theory); m.p. 162° (ethanol/DIP).

EXAMPLE 6
4-(3,4-Dimethoxyphenyl)-pyrrolidone-2-thione

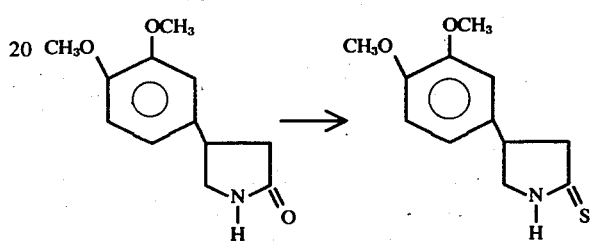

1.98 g. of 4-(3,4-dimethoxyphenyl)-2-pyrrolidone (9 mmol) and 5.4 g. of phosphorus pentasulfide (5.4 mmol) are suspended in a mixture of 9 ml. of acetonitrile and 9 ml. of glycol dimethyl ether. At room temperature and under agitation, 1.4 g. of sodium bicarbonate (18 mmol) is added thereto in small portions. While stirring for another 1.5 hours, the suspension is first dissolved, and shortly thereafter the desired 4-(3,4-dimethoxyphenyl)-pyrrolidone-2-thione is crystallized. The reaction mixture is poured into ice water and vacuum-filtered.

Yield: 1.57 g. (78% of theory); m.p. 151°–152° (ethanol).

Analogously, the following compounds are produced:
4-(3-isobutoxy-4-methoxyphenyl)-pyrrolidine-2-thione (6 a) and
4-(3-cyclopentyloxy-4-methoxyphenyl)-pyrrolidine-2-thione (6 b).

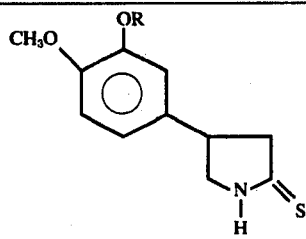

| R | Yield (% of Theory) | Melting Point (Recrystalliz- ing Agent) |
|---|---|---|
| 6 a  —CH$_2$—CH(CH$_3$)CH$_3$ | 68 | 102–104° (ethanol/W) |
| 6 b  —cyclopentyl | 42 | 109–111° (ethanol/W) |

EXAMPLE 7

A homogeneous mixture is prepared from the following components:

| | | |
|---|---|---|
| 20 | mg. | 4-(3,4-dimethoxyphenyl)-2-pyrrolidone |
| 65.5 | mg. | lactose |
| 32.2 | mg. | corn starch |
| 2.0 | mg. | poly-N-vinylpyrrolidone |
| 0.3 | mg. | magnesium stearate |
| 120.0 | mg. | | and this mixture is compressed, without previous granulation, to tablets with a breaking notch, weighing 120 mg.

EXAMPLE 8

Analogously to Example 7, the following mixture:

| | | |
|---|---|---|
| 5 | mg. | 4-(3-cyclopentyloxy-4-methoxyphenyl)-2-pyrrolidone |
| 105 | mg. | lactose |
| 8 | mg. | corn starch |
| 0.5 | mg. | magnesium stearate |
| 0.5 | mg. | "Aerosil" |
| 1.0 | mg. | talc |
| 120.0 | mg. | | is compressed to tablets having a final weight of 120 mg.

EXAMPLE 9

5 mg. of 4-(3-isobutoxy-4-methoxyphenyl)-2-pyrrolidone is dissolved in 2 ml. of castor oil/benzyl benzoate (4 : 6). This oily solution is intended for injection.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A pharamaceutical composition for the treatment of neurological and psychic disorders responsive to chlorpromazine therapy and characterized by one or more of the symptoms of anxiety, hostility, aggression, withdrawal, hallucination, thought-disturbances, delusion and agitation, comprising, in admixture with a pharmaceutically acceptable carrier, an amount per dosage unit from 0.05–20 mg. effective to reduce the symptoms of such disorders, of a 4-(polyalkoxyphenyl)-2-pyrrolidone of the formula

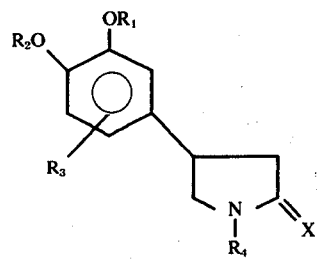

wherein $R_1$ and $R_2$ each are hydrocarbon of up to 18 carbon atoms or alkyl of 1–5 carbon atoms substituted by one or more halogen atoms or by one hydroxy, carboxy, alkoxy of 1–5 carbon atoms, alkoxycarbonyl of 1–5 carbon atoms in the alkoxy group, carboxamido, alkylcarboxamido, dialkylcarboxamido, carboxycyclicamido, amino, alkylamino, dialkyl or alkyleneimino, wherein alkyl in each instance is of 1–5 carbon atoms and wherein the nitrogen atom of the cyclicamido and alkyleneimino groups is a ring member of alkyleneimino of 4 to 7 members or $R_1$ or $R_2$ collectively are alkylene of 1–3 carbon atoms; $R_3$ is a hydrogen atom or methoxy; $R_4$ is a hydrogen atom, alkyl of 1–5 carbon atoms, phenyl, naphthyl, tolyl, xylyl or alkanoyl of 1–6 carbon atoms; and X is an oxygen atom or a sulfur atom.

2. A composition of claim 1 wherein X is O.
3. A composition of claim 1 wherein $R_2$ is methyl.
4. A composition of claim 3 wherein $R_4$ is H.
5. A composition of claim 4 wherein $R_3$ is H.
6. A composition of claim 5 wherein $R_1$ is hydrocarbon of up to 18 carbon atoms.
7. A composition of claim 1 wherein the pyrrolidone is 4-(3,4-dimethoxyphenyl)-2-pyrrolidone.
8. A composition of claim 1 wherein the pyrrolidone is 4-(2,3,4-trimethoxyphenyl)-2-pyrrolidone.
9. A composition of claim 1 where the pyrrolidone is 4-(3,4,6-trimethoxyphenyl)-2-pyrrolidone.
10. A composition of claim 1 wherein the pyrrolidone is 4-(3-methylenedioxyphenyl)-2-pyrrolidone.
11. A composition of claim 1 wherein the pyrrolidone is 4-(3,4-ethylenedioxyphenyl)-2-pyrrolidone.
12. A composition of claim 1 wherein the pyrrolidone is 4-(3-isobutoxy-4-methoxyphenyl)-2-pyrrolidone.
13. A composition of claim 1 wherein the pyrrolidone is 4-(3,4,5-trimethoxyphenyl)-2-pyrrolidone.
14. A composition of claim 1 wherein the pyrrolidone is 4-(3-ethoxy-4-methoxyphenyl)-2-pyrrolidone.
15. A composition of claim 1 wherein the pyrrolidone is 4-(3-propoxy-4-methoxyphenyl)-2-pyrrolidone.
16. A composition of claim 1 wherein the pyrrolidone is 4-(3-butoxy-4-methoxyphenyl)-2-pyrrolidone.

17. A composition of claim 1 wherein the pyrrolidone is 4-(3-hexyloxy-4-methoxyphenyl)-2-pyrrolidone.

18. A composition of claim 1 wherein the pyrrolidone is 4-(3-isopropoxy-4-methoxyphenyl)-2-pyrrolidone.

19. A composition of claim 1 wherein the pyrrolidone is 4-(3-[1-methylpropoxy]-4-methoxyphenyl)-2-pyrrolidone.

20. A composition of claim 1 wherein the pyrrolidone is 4-(3-isobutoxy-4-methoxyphenyl)-2-pyrrolione.

21. A composition of claim 1 wherein the pyrrolidone is 4-(3-allyloxy-4-methoxyphenyl)-2-pyrrolidone.

22. A composition of claim 1 wherein the pyrrolidone is 4-(3-[3-methyl-2-butenyloxy]-4-methoxyphenyl)-2-pyrrolidone.

23. A composition of claim 1 wherein the pyrrolidone is 4-(3-methoxymethoxy-4-methoxyphenyl)-2-pyrrolidone.

24. A composition of claim 1 wherein the pyrrolidone is 4-(3-diethylaminocarbonylmethoxy-4-methoxyphenyl)-2-pyrrolidone.

25. A composition of claim 1 wherein the pyrrolidone is 4-(3-[2-hydroxyethoxy]-4-methoxyphenyl)-2-pyrrolidone.

26. A composition of claim 1 wherein the pyrrolidone is 4-(3-[2,2,2-trifluoroethoxy]-4-methoxyphenyl)-2-pyrrolidone.

27. A composition of claim 1 wherein the pyrrolidone is 4-(3-benzyloxy-4-methoxyphenyl)-2-pyrrolidone.

28. A composition of claim 1 wherein the pyrrolidone is 4-(3-phenoxy-4-methoxyphenyl)-2-pyrrolidone.

29. A composition of claim 1 wherein the pyrrolidone is 4-(3-methoxy-4-ethoxyphenyl)-2-pyrrolidone.

30. A composition of claim 1 wherein the pyrrolidone is 4-(3-methoxy-4-butoxyphenyl)-2-pyrrolidone.

31. A composition of claim 1 wherein the pyrrolidone is 4-(3-methoxy-4-diethylaminocarbonylmethoxyphenyl)-2-pyrrolidone.

32. A composition of claim 1 wherein the pyrrolidone is 4-(3,4-dimethoxyphenyl)-1-methyl-2-pyrrolidone.

33. A composition of claim 1 wherein the pyrrolidone is 1-acetyl-4-(3,4-dimethoxyphenyl)-2-pyrrolidone.

34. A composition of claim 1 wherein the pyrrolidone is 4-(3,4-dimethoxyphenyl)-1-phenyl-2-pyrrolidone.

35. A composition of claim 1 wherein the pyrrolidone is 4-(3,4-dimethoxyphenyl)-pyrrolidone-2-thione.

36. A composition of claim 1 wherein the pyrrolidone is 4-(3-decyloxy-4-methoxyphenyl)-2-pyrrolidone.

37. A composition of claim 1 wherein the pyrrolidone is 4-(3-octadecyloxy-4-methoxyphenyl)-2-pyrrolidone.

38. A composition of claim 1 wherein the pyrrolidone is 4-(3-[2-methylbutyl]-oxy-4-methoxyphenyl)-2-pyrrolidone.

39. A composition of claim 1 wherein the pyrrolidone is 4-(3-neopentyloxy-4-methoxyphenyl)-2-pyrrolidone.

40. A composition of claim 1 wherein the pyrrolidone is 4-(3-isopentyloxy-4-methoxyphenyl)-2-pyrrolidone.

41. A composition of claim 1 wherein the pyrrolidone is 4-(3-[2-propinyl]-oxy-4-methoxyphenyl)-2-pyrrolidone.

42. A composition of claim 1 wherein the pyrrolidone is 4-(3-cyanomethyloxy-4-methoxyphenyl)-2-pyrrolidone.

43. A composition of claim 1 wherein the pyrrolidone is 4-(3-cyclobutoxy-4-methoxyphenyl)-2-pyrrolidone.

44. A composition of claim 1 wherein the pyrrolidone is 4-(3-cyclopentyloxy-4-methoxyphenyl)-2-pyrrolidone.

45. A composition of claim 1 wherein the pyrrolidone is 4-(3-cyclohexyloxy-4-methoxyphenyl)-2-pyrrolidone.

46. A composition of claim 1 wherein the pyrrolidone is 4-(3-[3-methylcyclopentyl]-oxy-4-methoxyphenyl)-2-pyrrolidone.

47. A composition of claim 1 wherein the pyrrolidone is 4-(3-[2-methylcyclopentyl]-oxy-4-methoxyphenyl)-2-pyrrolidone.

48. A method of treating neurological and psychic disorders responsive to chlorpromazine therapy and characterized by one or more of the symptons of anxiety, hostility, aggression, withdrawal, hallucination, thought-disturbances, delusion and agitation, which comprises administering to a patient exhibiting the symptoms of such a disorder an amount of a composition of claim 1 effective to reduce the symptoms.

49. A composition of claim 1 wherein X is S.

50. A composition of claim 1 wherein the pyrrolidone is 4-(3-cyclopropylmethoxyloxy-4-methoxyphenyl)-2-pyrrolidone.

51. A composition of claim 1 wherein the pyrrolidone is 4-(3-cyclopentylmethyloxy-4-methoxyphenyl)-2-pyrrolidone.

52. A composition of claim 1 wherein the pyrrolidone is 4-(3-isobutoxy-4-methoxyphenyl)-pyrrolidene-2-thione.

53. A composition of claim 1 wherein the pyrrolidone is 4-(3-methallyloxy-4-methoxyphenyl)-2-pyrrolidone.

54. A composition of claim 1 wherein the pyrrolidone is 4-(4-propinyloxy-3-methoxyphenyl)-2-pyrrolidone.

55. A composition of claim 1 wherein the pyrrolidone is 4-(4-cyclopentyloxy-3-methoxyphenyl)-2-pyrrolidone.

56. A composition of claim 1 wherein the pyrrolidone is 4-(3,4-diethoxyphenyl)-2-pyrrolidone.

57. A composition of claim 1 wherein the pyrrolidone is 4-(3,4-diisobutoxyphenyl)-2-pyrrolidone.

58. A composition of claim 1 wherein the pyrrolidone is 4-(3-cyclopentyloxy-4-methoxyphenyl)-pyrrolidine-2-thione.

* * * * *